United States Patent [19]

Günther

[11] 4,425,276

[45] Jan. 10, 1984

[54] PROCESS FOR THE SEPARATION OF OIL AND/OR PHOSPHATIDYLETHANOLAMINE FROM ALCOHOL SOLUBLE PHOSPHATIDYLCHOLINE PRODUCTS CONTAINING THE SAME

[75] Inventor: Bernd-Rainer Günther, Bergheim-Fliesteden, Fed. Rep. of Germany

[73] Assignee: A. Nattermann & Cie GmbH, Cologne, Fed. Rep. of Germany

[21] Appl. No.: 326,379

[22] Filed: Dec. 1, 1981

[30] Foreign Application Priority Data

Dec. 13, 1980 [DE] Fed. Rep. of Germany ....... 3047048

[51] Int. Cl.$^3$ ............................. A23J 7/00; C07F 9/02
[52] U.S. Cl. .................................................. 260/403
[58] Field of Search ........................................ 260/403

[56] References Cited

U.S. PATENT DOCUMENTS

| | | | |
|---|---|---|---|
| 2,276,316 | 3/1942 | Kraybill et al. | 260/403 |
| 2,724,649 | 11/1955 | Julian et al. | 99/123 |
| 3,031,478 | 8/1962 | Klenk et al. | 260/403 |
| 3,197,368 | 7/1965 | Lappe et al. | 260/403 X |
| 3,268,335 | 8/1966 | Circle et al. | 99/15 |
| 3,325,291 | 6/1967 | Eikermann et al. | 260/403 X |
| 3,544,605 | 12/1970 | Betzing et al. | 260/403 |
| 3,661,946 | 5/1972 | Purdue | 260/403 |
| 3,869,482 | 3/1975 | Wolfe | 260/403 |
| 4,235,793 | 11/1980 | Betzing | 260/403 |

FOREIGN PATENT DOCUMENTS

| | | | |
|---|---|---|---|
| 1053299 | 3/1959 | Fed. Rep. of Germany | 260/403 |
| 1905253 | 8/1970 | Fed. Rep. of Germany | 260/403 |
| 79916 | 2/1971 | German Democratic Rep. | 260/403 |
| 1113241 | 5/1968 | United Kingdom . | |

*Primary Examiner*—Thomas A. Waltz
*Attorney, Agent, or Firm*—Pearne, Gordon, Sessions, McCoy, Granger & Tilberry

[57] ABSTRACT

The present invention is related to a new process for the separation of oil and/or phosphatidylethanolamine from alcohol soluble phosphatidylcholine products containing the same thus producing a highly purified phosphatidylcholine, by chromatography on silicic acid gel in a lower alkanol containing 1 to 4 carbon atoms as solvent and/or eluant.

5 Claims, No Drawings

PROCESS FOR THE SEPARATION OF OIL AND/OR PHOSPHATIDYLETHANOLAMINE FROM ALCOHOL SOLUBLE PHOSPHATIDYLCHOLINE PRODUCTS CONTAINING THE SAME

The present invention is related to a new process for the separation of oil and/or phosphatidylethanolamine from alcohol soluble phosphatidylcholine products containing the same, thus producing a highly purified phosphatidylcholine, by chromatographic adsorption on silicic acid gel.

The crude phosphatides from plant origin recovered in the production of edible oil besides phosphatidylcholine contain phosphatidylethanolamine and mono-, di- and triglycerides (hereinafter referred to as oils) as well as phosphatidylinosite and other phosphorus containing glycerol esters and products such as peptides, amino acids, sterines, sterineesters, free fatty acids and hydrocarbon derivatives. For use in the pharmaceutical industry a highly purified phosphatidylcholine free of oil and phosphatidylethanolamine is particularly desired.

For separating the components contained in the crude phosphatide several processes are already known. In general, the crude phosphatide of plant origin at first is treated with acetone to be deoiled (U.S. Pat. Nos. 3,031,478 and 3,268,335) and then in a second step extracted with ethanol (U.S. Pat. No. 2,724,649). In a third step the phosphatide fraction soluble in ethanol is subjected to adsorption chromatography at temperatures not exceeding 35° C. (U.S. Pat. No. 3,031,478). During oil separation by means of acetone, small amounts of undesired acetone derivatives such as mesityloxide, diacetone alcohol, phorone and others are formed. The separation of these toxic derivatives which are particularly disturbing by their very characteristic smell is either most burdensome or even impossible. Furthermore, during removal of oil by means of acetone, an increase of peroxide formation occurs which has known undesirable physiological properties. The alcoholic extraction of crude phosphatides of plant origin yields an oil-containing phosphatide fraction (U.S. Pat. No. 4,235,793, British Pat. No. 1,113,241 and U.S. Pat. No. 3,661,946) allowing recovery of an oil-containing phosphatidylcholine free of phosphatidylethanolamine by chromatographic purification at room temperature. A further invention owned by the assignee herein (U.S. patent application Ser. No. 06/269,805) allows separation of the oil by the addition of small amounts of water to obtain a highly purified oil-free phosphatidylcholine. However, this aqueous oil removal which is suitable for the production of certain phosphatide fractions, represents a threestep process (extraction, chromatography, oil-removal) in the production of an oil-free phosphatidylcholine. A further disadvantage is the removal of water from the ethanol solvent.

It is a prerequisite for the production of highly purified phosphatidylcholine to chromatographically separate the by-products contained in the ethanol-soluble phosphatide fraction. Aluminum oxide is mostly used as adsorbent. Purification occurs both on a column and by stirring with the adsorbent, in both cases at room temperature.

For purification on a technical scale, basic aluminum oxide is used. Chromatographic adsorption is carried out at room temperature. Since the aluminum oxide after chromatographic adsorption is loaded with the impurities, in particular with phosphatidylethanolamine, it has to be discarded. A further disadvantage is the formation of lysophosphatidylcholine during chromatography (O. Renkonen, J. Lipid.Res., vol. 3, pgs. 181 to 183 (1962), D. Van Damme et al., Int. Symp. Chromatogr. Elektrophoresis, 5th vol., 1968 (published 1969), pgs. 268 to 268 to 278). Chromatography on silicic acid gel up to now only has been used analytically or on a laboratory scale. Thus, phosphatides in hexane solution are not adsorbed on silicic acid gel (Japanese application 77012202, U.S. Pat. No. 3,869,482) while they are kept back in alcoholic solution on silicic acid gel (H. Richter et al., Pharmazie, 1977, vol. 32 (3), p. 164). This difference in property is explained with the formation of lipophilic, polymolecular phosphatide micells in hexane over the phosphatides present as single molecules in alcohol. Chromatography again is carried out at room temperature. The separation and selective desorption of the phosphatides occurs either with alcohol/ammonia (Japanese patent specification 49093400) or with mixtures of chloroform and methanol (C. H. Lea et al., Biochem. J. vol. 60 (1965), pgs. 353 to 363) or with chloroform/methanol/water (East German Patent No. 79 916) when using alcoholic phosphatide solutions. However, it was not possible to transfer these procedures to a technical scale since mixtures with toxic products such as ammonia or chloroform always have been used as eluants and the recovery and removal thereof from the final lecithine.

Phosphatidylcholine crude products as they are in trade, and particular from soybeans, represent products which have been obtained by extraction with alcohol and which are soluble in alcohol and contain as main by-product oil and phosphatidylethanolamine. However, there are also phosphatidylcholine crude products which as described contain only one or the other of these two main by-products. It is an object of the present invention to provide a technical process for the separation of oils and/or phosphatidylethanolamine from alcohol soluble phosphatidylcholine crude products containing the same and to produce a highly purified phosphatidylcholine substantially free of these side products. All of the known processes have the disadvantage that they comprise complicated procedural steps for obtaining a pure phosphatidylcholine free of oils and phosphatidylethanolamine, comprising the formation and the remainder to toxic products. Furthermore, the aluminum oxide used up to now as adsorbent in the chromatographic purification had to be discarded.

It has been surprisingly found that when starting from alcohol soluble phosphatide fractions containing oils and/or phosphatidylethanolamine, such may be purified by means of column chromatography using silicic acid gel as adsorbent at an elevated temperature resulting in highly purified phosphatidylcholine free of oils and phosphatidylethanolamine. The process of the present invention for the separation of oils and/or phosphatidylethanolamine from such alcohol soluble phosphatidylcholine crude products with the formation of highly purified phosphatidylcholine free of oils and phosphatidylethanolamine is characterized in that the solution of an alcohol soluble phosphatidylcholine containing oils and/or phosphatidylethanolamine in a lower alkanol containing from 1 to 4 carbon atoms or a mixture of several such alkanols, possibly admixed with up to 20% by volume of water, at a temperature ranging from 40° to 90° C. is put on a column of silicic acid gel, the column is eluated at this temperature with a lower alkanol containing from 1 to 4 carbon atoms or a mixture of several such lower alkanols, possibly containing up to 20% by volume of water, the collected preeluant containing the oil and/or phosphatidylethanolamine is separated and, separately herefrom, the main eluant containing the pure phosphatidylcholine is collected and the solvent is separated in usual manners from the main eluant.

Preferably, the solvent is put to the silicic acid gel column and this column is eluated at a temperature ranging from 60° to 90° C., most preferably from 60° to 70° C. Preferably, the used solvent is applied also as eluant making the present process particularly simple. The preferred lower alkanol having from 1 to 4 carbon atoms is ethanol.

The amount of preeluant depends upon the phosphatidylcholine starting product. It may be simply determined by known analytical methods from which time of eluation the eluate is free of the by-products to be separated and practically only contains phosphatidylcholine. According to general experience with various phosphatidylcholine products and the application of the present process, the preeluate is about 20 to 25% of the total volume of the eluate. Depending upon the phosphatidylcholine starting product, the preeluate further contains the other usually present by-products such as sterines, sterine derivatives, glycolipids and phospholipids. They can be further used in known manners.

The silicic acid gels are known products, useful in chromatography, and have varying grain size. They furthermore can be pressed silicic acid gel. Such silicic acid gel products may be activated or deactivated. Most preferred are neutral silicic acid gel products.

The process according to the present invention may be carried out at normal pressure or at higher pressures. It is a particular advantage of the process of the present invention that the silicic acid gel may repeatedly be used. All impurities are contained in the preeluate. After collection of the main eluate there is only adsorbed a small amount of phosphatidylcholine.

A further advantage of silicic acid gel used in the present process is the high amounts which can be adsorbed. Thus, carrying out the present process with 100 parts by weight of silicic acid gel about 60 parts by weight of solid material may be separated from the alcohol soluble phosphatide fraction.

The phosphatidylcholine starting products may be obtained by extraction with alcohol from for instance soybeans, peanuts, sun-flowers or rape. The phosphatide is dissolved with a lower aliphatic alcohol such as methanol, ethanol, n-propanol or sec. propanol, in particular with 94 to 96% by volume of ethanol. Sedimented products are separated in usual manners and the clear alcohol solution or a concentrate thereof is used in the process according to the present invention. The solvent used for extraction may be removed completely and the resulting solid product may be again dissolved in one or several lower alcohols containing from 1 to 4 carbon atoms and possibly containing up to 20% by volume of water.

The preparation of pure phosphatidylcholine from phosphatidylcholine crude products containing both oils and phosphatidylethanolamine according to the present process in comparison to known processes is substantially simplified by removing the oils and separating phosphatidylethanolamine in one single step. A further advantage of the process according to the present invention which occurs when starting from phosphatidylcholine products both by-products have been already separated in other manners, is the reusability of the used silicic acid gel.

EXAMPLES

Analysis

The phosphatides are analysed by thin layer chromatography. The oil content is equal the products which may be dialysed. The water content is determined according to Kark Fischer and the ethanol content is determined by gas chromatography.

Column chromatography

There is used a usual heatable column (inner diameter 4.5 cm., length 37 cm.). The column is combined with a heat exchanger in order to guarantee equal column temperature and starting temperature. The column is prepared from a slurry of 200 g. of silicic acid gel (Merck, Darmstadt/Germany) in the applied solvent. The silicic acid gel may be reused after used in the present process.

Starting materials

Crude soybean phosphatide is extracted at 35° C. with 95% ethanol using 1 part by weight of crude phosphatide to 2.5 parts by weight of ethanol. The sedimented solid material is separated at room temperature from the supernatant ethanol phase.

The ethanol phase is evaporated. The resulting solid material showed the following analysis:

| Phosphatidylcholine (PC) | 43% |
| Phosphatidylethanolamine (PE) | 12% |
| Oils | 21% |

This solid material was used in the following Examples 1 to 4 as starting material.

The starting material used in Example 5 was prepared as follows:

Oils are separated from crude soybeans phosphatide with acetone. The resulting product is extracted with 95% by volume of ethanol. The phosphatide fraction soluble in ethanol is evaporated and analysed:

| PC content | 52% |
| PE content | 20% |

The phosphatidylcholine product containing oils, but free of phosphatidylethanolamine used in Example 6 has been prepared in accordance to Example 3 of German Offenlegungsschrift 2 718 797 and showed the following analysis:

| PC content | 68% |
| Oil content | 28% |

EXAMPLE 1

118 g. of solid material are dissolved in 275 g. of 95% ethanol. This solvent is used also as eluant, producing 4 l. of eluate. The applied temperature of the column and solution was 70° C. 1 l. of preeluate is collected, whereafter a total of 3 l. of the main eluate are collected. The main eluate is evaporated and analysed:

| Yield in total solids | 34% of the theoretical |
| --- | --- |
| PC content | 92% |
| PE content | <1% |
| Oil content | <1% |
| PC yield calculated to the starting solid material | 72% of the theoretical. |

EXAMPLE 2

118 g. are dissolved in 1280 g. of 95% ethanol, the solution is put to the column. 95% ethanol is used as eluant. A total of 4 l. of eluate is collected. Adsorption and elution occurs at 65° C.

There are at first collected 2 l. of preeluate, thereafter 2 l. of main eluate. The main eluate is evaporated and analysed:

| Yield in solid material | 22% of the theoretical |
| --- | --- |
| PC content | 90% |
| PE content | <1% |
| Oil content | <1% |
| PC yield calculated to the starting solid material | 46% of the theoretical. |

EXAMPLE 3

There are put on to the column 118 g. of solid material dissolved in 29 g. of 95% ethanol. This solvent is used also as eluant to produce a total of 4 l. of eluate. The temperature of the column was 65° C. There was collected 0.5 l. of preeluate and 3.5 l. of main eluate. The main eluate was evaporated and analysed:

| Yield in solid material | 38% of the theoretical |
| --- | --- |
| PC content | 87% |
| PE content | <1% |
| Oil content | <1% |
| PC yield calculated to the solid material | 77% of the theoretical. |

EXAMPLE 4

There were put to the column 118 g. of solid material dissolved in 50 g. of n-propanol. n-Propanol was first used for a preeluate of 1 l. Thereafter 85% aqueous n-propanol was used to collect 3 l. of eluate. The temperature of the column was 90° C.

After collecting 1 l. of preeluate, 3 l. of main eluate (in 85% aqueous n-propanol) were collected. The main eluate was evaporated and analysed:

| Yield in solid material | 45% of the theoretical |
| --- | --- |
| PC content | 86% |
| PE content | <1% |
| Oil content | <1% |
| Yield in PC, calculated to solid material | 90% of the theoretical |

EXAMPLE 5

There were put to the column 110 g. of solid material in 40 g. of 95% of ethanol. This solvent was used also as eluant to produce 4 l. of eluate. The temperature of the column was 65° C.

After collecting 1 l. of preeluate, there were collected 3 l. of main eluate. The main eluate was evaporated and analysed:

| Yield in solid material | 34% of the theoretical |
| --- | --- |
| PC content | 92% |
| PE content | <1% |
| Oil content | <1% |
| Yield in PC, calculated to the solid material | 60% of the theoretical. |

EXAMPLE 6

There were put to the column 80 g. of solid material dissolved in 30 g. of 95% ethanol. This solvent was also used as eluant to produce a total of 4 l. of eluate. The temperature of the column was 65° C.

After collecting 1 l. of preeluate, there were collected 3 l. of main eluate. The main eluate was evaporated and analysed:

| Yield in solid material | 44% of the theoretical |
| --- | --- |
| PC content | 93% |
| Oil content | <1% |
| Yield in PC, calculated to the solid material | 75% of the theoretical. |

What I claim is:

1. Process for the separation of oil and/or phosphatidylethanolamine from alcohol soluble phosphatidylcholine products containing the same, thus producing a phosphatidylcholine free of oil and phosphatidylethanolamine characterized in that the solution of the alcohol soluble phosphatidylcholine product containing the oil and/or phosphatidylethanolamine, in a lower alkanol containing from 1 to 4 carbon atoms or in a mixture of several of such lower alkanols, said lower alkanol or mixture of alkanols being possibly admixed with up to 20% by volume of water, is put to the head of a chromatography column of silicic acid gel at a temperature ranging from 40° to 90° C., eluating the column at this temperature with a lower alkanol having from 1 to 4 carbon atoms or a mixture of several of such lower alkanols, said lower alkanol or mixture of alkanols being possibly containing up to 20% by volumn of water, recovering at first a prefraction containing the oil and/or phosphatidylethanolamine to be separated and, separate therefrom, the main fraction containing the pure phosphatidylcholine, and separating the solvent from the main fraction in usual manners.

2. Process according to claim 1 characterized in that both the addition of the solvent of the phosphatidylcholine product to be purified to the silicic acid gel column as well as the eluation thereof is effected at a temperature ranging from 60° to 70° C.

3. Process according to claim 1 or 2, characterized in that the same solvent is used for dissolving the phosphatidylcholine product to be purified and for the eluation of the column.

4. Process according to claim 1, characterized in that ethanol is used as the lower alkanol having from 1 to 4 carbon atoms.

5. Process according to claim 3, characterized in that ethanol is used as the lower alkanol having from 1 to 4 carbon atoms.